| United States Patent [19] | [11] Patent Number: 4,818,703 |
|---|---|
| Pizzolante | [45] Date of Patent: Apr. 4, 1989 |

[54] STABILIZED ALKALINE PICRATE REAGENT FOR JAFFE CREATININE DETERMINATION

[76] Inventor: John M. Pizzolante, 4 Todd Rd., Woburn, Mass. 01801

[21] Appl. No.: 78,029

[22] Filed: Jul. 27, 1987

Related U.S. Application Data

[63] Continuation of Ser. No. 790,456, Oct. 23, 1985, abandoned.

[51] Int. Cl.⁴ ............................................. G01N 33/70
[52] U.S. Cl. ...................................... 436/98; 436/106
[58] Field of Search ................................. 439/98, 106

[56] References Cited

U.S. PATENT DOCUMENTS

| | | | |
|---|---|---|---|
| 3,557,018 | 1/1971 | Scheuerbrandt | 436/98 |
| 3,682,586 | 8/1972 | Ertingshausen et al. | 436/98 X |
| 3,705,013 | 12/1972 | Dewhurst | 436/98 |
| 3,723,063 | 3/1973 | Jones et al. | 436/98 |
| 3,751,381 | 8/1973 | Megraw et al. | 252/408 |
| 3,876,375 | 4/1975 | Maurukas | 252/408 |
| 3,891,573 | 6/1975 | Stary et al. | 252/408 |
| 3,894,843 | 7/1975 | Jarvis | 436/98 |
| 4,056,485 | 11/1977 | Adolf et al. | 252/408 |
| 4,102,810 | 7/1978 | Armstrong | 252/408 |
| 4,111,657 | 9/1978 | Denney et al. | 436/98 |
| 4,121,905 | 10/1978 | Maurukas | 252/408 X |
| 4,153,511 | 5/1979 | Modrovich | 436/176 X |
| 4,158,544 | 6/1979 | Louderback | 436/98 X |
| 4,189,401 | 2/1980 | Louderback | 252/408 |
| 4,372,874 | 2/1983 | Modrovich | 436/176 |
| 4,389,490 | 6/1983 | Crews et al. | 436/17 |
| 4,390,632 | 6/1983 | Carter, II | 436/10 |
| 4,529,708 | 7/1985 | Stephens | 436/98 |

FOREIGN PATENT DOCUMENTS

| | | | |
|---|---|---|---|
| 741316 | 5/1970 | Belgium | 436/98 |
| 20332 | 7/1972 | Japan | 436/98 |
| 110383 | 8/1975 | Japan | 436/98 |
| 69692 | 6/1978 | Japan | 436/98 |
| 150195 | 11/1979 | Japan | 436/98 |
| 29718 | 3/1980 | Japan | 436/98 |

OTHER PUBLICATIONS

Bromberg, Clin. Chem., 30, 281–283 (1984).
Posner, Clin. Chem., 30, 1105 (1984).
van Staden, Fresenius Z., Anal. Chem., 315, 141–144 (1983).
Bauer, "Clinical Laboratory Methods", 9th ed., p. 490 (1982).
Yatzidis, Clin. Chem., 28, 384 (1982).
Haeckel, Clin. Chem., 27, 179–183 (1981).
Diamandis, Clin. Chem., 27, 455–457 (1981).
Masson, Clin. Chem., 27, 18–21 (1981).
Schifreen, Clin. Chem., 27, 196–197 (1981).
Bowers, Clin. Chem., 26, 555–561 (1980).
Narayanan, Clin. Chem., 26, 1119–1126 (1980).
Jury, Clin. Chem., 25, 1674 (1979).
Kammeraat, Clin. Chem. Acta, 84, 119–128 (1978).
Shoucri, Clin. Chem., 23, 1527–1530 (1977).
Blass, Microchem., J. 19, 1–7 (1974).
Medzihradsky, Lab. Pract. (GB), 23, 481–482 (1974).
Bray's Clinical Laboratory Methods, Revised by Bauer, Ackermann, and Toro, C. V. Mosby Company (1968).
Peters and van Slyke, Quan. Clin. Chem., vol. II, Chapter XV, pp. 597–604 (1965).
Toro and Ackermann, "Practical Clinical Chemistry", Little, Brown Company, pp. 151–155.
U.S. Naval Medical School, "Physiological Chemistry", pp. 168–170 (1951), Clark, Anal. Chem., 21, 1218–1221 (1949).

*Primary Examiner*—Robert Spitzer
*Attorney, Agent, or Firm*—Weingarten, Schurgin, Gagnebin & Hayes

[57] ABSTRACT

The alkaline picrate reagent solution employed in the Jaffe procedure for determining the presence and concentration of creatinine is stabilized for at least one year to permit long shelf life and improve the efficiency of creatinine testing. Stability is achieved by the addition of 5 to 20% by volume of a low molecular weight alcohol such as methanol.

10 Claims, No Drawings

STABILIZED ALKALINE PICRATE REAGENT FOR JAFFE CREATININE DETERMINATION

This application is a continuation of application Ser. No. 790,456, filed Oct. 23, 1985, now abandoned.

FIELD OF THE INVENTION

This invention relates to alkaline picrate analytical reagents for use in the determination of creatinine by the Jaffe reaction, and more particularly, to stabilization of such alkaline picrate analytical reagent solutions.

BACKGROUND OF THE INVENTION

The analytical determination of creatinine in urine, serum, or plasma is a widely used and extremely important clinical test for renal dysfunction. It is generally accepted that creatinine clearance is the best measure of glomerular filtration rate. Creatinine levels are also known to vary as a function of disorders such as muscular dystrophy and hypothyroidism.

The presence and concentration of creatinine in these body fluids is most frequently determined by the Jaffe reaction, in which creatinine reacts with picric acid in the presence of excess hydroxide to produce a red color. Many variations of the method have been developed to minimize the effects of numerous interferring materials which are known to be present in real samples.

In the Jaffe-derived procedures for the determination of creatinine, it is generally recommended that the picric acid and sodium hydroxide reagent solutions be stored separately and added individually to the solution to be tested just before the creatinine test, or if the picric acid and sodium hydroxide solutions are premixed to form the alkaline picrate reagent, that this solution should be used immediately or within a very short time. This is because the mixed alkaline picrate solution has a short shelf life. Examples of typical literature statements in this regard are the following, which clearly demonstrate that in the Jaffe alkaline picrate reaction for the determination of creatinine, regardless which of the many variations of the method are employed, stability of the alkaline picrate reagent has been a continuing problem.

a. In the laboratory manual entitled "Physiological Chemistry," published by the United States Naval Medical School in 1951, it is stated on page 170 that the alkaline picrate solution "must be made just prior to use and discarded after standing one hour."

b. In "Practical Clinical Chemistry" by Toro and Ackermann, the procedure for serum states "to each tube add 1 ml of picric acid solution, mix, and add 1 ml of the sodium hydroxide solution."

c. In "Quantitative Clinical Chemistry," Volume 2, by Peters and Van Slyke, Chapter XV, it is stated on page 604, "to the blood filtrate add 5 cc and to the standard solution 10 cc of the freshly prepared alkaline picrate."

d. In "Bray's Clinical Laboratory Methods," revised by Bauer, Ackermann, and Toro, published by the C. V. Mosby Company in 1968, it is stated on page 315, "to each tube add 1 ml picric acid and 1 ml sodium hydroxide solution. Mix, and after standing at room temperature for 20 minutes, read in a photometer."

e. In the article by Shoucri and Pouliot in "Clinical Chemistry," 23, p1527 (1977), it is stated on page 1527 that the mixed alkaline picrate reagent is stable for one day.

f. In the U.S. Pat. No. 4,111,657 by Denney et al, issued in 1978, it is stated in column 6, lines 7–12 that the mixed alkaline picrate reagent has a demonstrated stability in excess of five days when stored at room temperature and protected from light.

g. In the article by Kammeraat, in "Clinica Chimica Acta," 84, p119 (1978), it is stated on page 121 that the mixed alkaline picrate reagent can be used 30 minutes after mixing and is stable for at least one week at room temperature in the dark.

h. In a letter by Jury and Ward in "Clinical Chemistry," 25, p1674 (1979), a recipe for an alkaline buffer containing sodium hydroxide and several other chemicals is given. This buffer is mixed with saturated picric acid solution to prepare a working creatinine reagent. However, in a later communication by Schifreen, Sindab, Bologna, Cameron, and Burnett, in "Clinical Chemistry," 27, p196 (1981), it is stated that a white precipitate forms after about one week of storage of this reagent, making it unusable. These authors recommend adding diethylamine to the mixture to prevent formation of this precipitate for at least one month.

i. In the "Proposed Selected Method" submitted by Haeckel and Hannover, published in "Clinical Chemistry," 27, p179 (1981), it is stated on page 179 that the mixed alkaline picrate solution is stable for at least three months if stored in a dark bottle.

j. In "Clinical Laboratory Methods" by John Bauer, ninth edition, published by the C. V. Mosbey Company in 1982, it is stated on page 490 that the picric acid reagents are mixed just before use.

k. In the communication by Yatzidis, Frangos-Plemenos, and Koutsicos, published in "Clinical Chemistry," 28, p384 (1982), it is stated that the alkaline picrate reagent is prepared by mixing picric acid solution with sodium hydroxide solution just before use.

l. In the article by Bromberg, Pollard, Cheng, and Romaschin, published in "Clinical Chemistry," 30, p281 (1984), it is stated on page 281 that the Technicon RA 1000 creatinine reagent can only be used for four hours after preparation, and that the Beckmann creatinine reagent is stable for one week.

m. In the communication by Posner published in "Clinical Chemistry," 30, p1105 (1984), it is stated with regard to the above-listed publication by Bromberg that the correct statement with regard to the Beckmann creatinine reagent is "the Beckmann alkaline-picrate reagent is a special purpose solution . . . from date of preparation for use, working reagent is stable for 30 days at ambient temperature."

This well documented instability of the alkaline picrate reagent solution is not to be confused with the relatively good stability of picric solutions, either as picric acid or as sodium picrate produced by neutralization of an initial picric acid solution. The alkaline picrate solutions which are the subject of the present invention always contain a substantial molar excess of base relative to the picric acid employed.

In view of the instability of alkaline picrate solutions and the concomitant necessity for preparing such solutions as needed, or at least with some frequency, it would be very desirable to have stable alkaline picrate solutions available. Such stable solutions would eliminate the need to prepare fresh reagent regularly, thereby saving substantial analytical time, and would also assure maximum reproducability of analytical results.

SUMMARY OF THE INVENTION

The deficiencies of the presently-employed alkaline picrate solutions are remedied in the present invention, which provides stable solutions of alkaline picrate with a long shelf life and which are suitable for use in any of the various modifications of the Jaffe reaction for the determination of creatinine.

In accordance with the teaching of the present invention alkaline picrate solutions are stabilized for periods of at least one year by mixing picric acid and excess alkali hydroxide in an aqueous alcohol solution. A low molecular weight alcohol is preferred, and methanol is especially preferred.

Thus, by means of the present invention alkaline picrate solutions for the determination of creatinine are prepared to contain a small amount of a low molecular weight alcohol. These premixed reagent solutions have a shelf life of up to at least a year after their preparation, thus reducing the preparative work load of the clinical laboratory performing creatinine testing and providing more consistent analytical results than were formerly possible.

DETAILED DESCRIPTION OF THE INVENTION

In accordance with the present invention, alkaline picrate solutions in which the concentrations of picric acid and alkali metal hydroxide are as called for by any of the variations of the Jaffe process are stabilized for at least a year by the addition of from 5 to 20% by volume of a low molecular weight alcohol containing from 1 to 4 carbon atoms. A preferred alcohol is methanol. Other suitable alcohols are ethanol, n-propanol, n-butanol, and isobutanol. Stabilizing agents other than methanol generally reduce the sensitivity of the analytical determination of creatinine slightly relative to methanol, but nevertheless stabilize the alkaline picrate reagent.

The alkali metal hydroxide employed is generally sodium hydroxide, but other materials such as potassium hydroxide and lithium hydroxide will also function.

The stabilized alkaline picrate reagent is prepared by mixing solutions of picric acid and an alkali metal hydroxide wherein either one or both of the individual solutions contain alcohol at a concentration such that upon combination of the individual solutions a final solution containing the appropriate amount of alcohol is obtained. Alternatively, aqueous solutions of picric acid and hydroxide may be combined and then diluted appropriately by alcohol or an aqueous alcohol solution. It is also possible to prepare the final solution directly by dissolution of the appropriate amounts of picric acid and hydroxide in a methanol-water solvent. The stabilized alkaline picrate solution can be prepared in any other convenient manner, a specific order of the combination of reagents not being essential.

EXPERIMENTAL SECTION

Creatinine analyses were performed on serum samples employing both methanol-stabilized alkaline picrate reagent and ordinary alkaline picrate reagent freshly prepared by the mixing of picric acid and sodium hydroxide solutions. Analyses were performed in parallel to permit a comparison of the methanol-stabilized alkaline picrate reagent with an ordinary alkaline picrate reagent on the same samples and by the same method.

The experimenrtal methanol-stabilized alkaline picrate reagent was prepared by mixing 5 parts by volume of a saturated aqueous solution of picric acid with 1 part by volume of a 10% weight to volume NaOH solution prepared in aqueous methanol containing 60 parts by volume of ACS-grade methanol and 40 parts by volume of water. The methanol stabilized alkaline picrate reagent was stored at room temperature throughout the testing period of 499 days.

The reference alkaline picrate reagent was prepared fresh daily by mixing 5 parts by volume of a saturated aqueous solution of picric acid with 1 part by volume of a 10% weight to volume aqueous NaOH solution.

Absorbance measurements were made on a spectrophotometer at a wavelength of 510 nm. Any spectrophotometer capable of reading absorbance at this wavelength and having a band width of less than 10 nm, stray light of less than 0.5%, and wavelength accuracy of ±3 nm will suffice for the determination. Samples, the creatinine levels of which were to be measured, were maintained at a constant temperature in the range of 24°-37° C.

Three ml of alkaline picrate reagent (stabilized with methanol or unstabilized, depending on the test being run) were placed in a cuvette or small test tube and allowed to equilibrate for a period of five minutes at a predetermined temperature in the range 24°-37° C. One hundred microliters of sample, creatinine standard, or control solution having a known level of creatinine was then added to the unstabilized or methanol-stabilized alkaline picrate solution. The reagents were mixed, and timing of the reaction was started. After 20 seconds the absorbance at 510 nm was read and recorded. The solution being analyzed was maintained at constant temperature, and a second absorbance reading was taken exactly 60 seconds after the first. The first absorbance reading was subtracted from the second absorbance reading to give an absorbance corresponding to the concentration of creatinine in the solution. The control solution was a serum sample having a creatinine assay of 5.2±1.0 mg/dl. The standard was a serum solution containing 1.0 mg/dl of creatinine. This method was found to give a linear response to creatinine levels up to 11.0 mg/dl. Concentrations of unknown and control solutions were determined by multiplying the measured absorbance of the unknown solution by the ratio of the concentration of an appropriate creatinine standard divided by the absorbance given by that standard. The results of the comparative tests are shown in Table I below.

TABLE I

Analytical Data for Creatinine Determinations Using Methanol-Stabilized Alkaline Picrate Reagent and Freshly-Prepared Non-Stabilized Alkaline Picrate Reagent

| Day | Solution | Stabilized Reagent: Measured Absorbance | Stabilized Reagent: Calculated Concentration (mg/dl) | Unstabilized Reagent: Measured Absorbance | Unstabilized Reagent: Calculated Concentration (mg/dl) |
|---|---|---|---|---|---|
| 1 | 1.0 std. | 0.032 | — | 0.038 | — |
| 1 | unknown | 0.050 | 1.5 | 0.058 | 1.5 |
| 45 | 1.0 std. | 0.035 | — | 0.030 | — |
| 45 | unknown | 0.14 | 4.0 | 0.16 | 4.2 |
| 111 | 1.0 std. | 0.038 | — | 0.030 | — |
| 111 | unknown | 0.060 | 1.6 | 0.048 | 1.4 |
| 111 | unknown | 0.07 | 1.8 | 0.068 | 1.9 |
| 156 | 1.0 std. | 0.035 | — | 0.032 | — |
| 156 | unknown | 0.05 | 1.4 | 0.04 | 1.3 |
| 156 | unknown | 0.14 | 4.0 | 0.135 | 4.2 |

TABLE I-continued

Analytical Data for Creatinine Determinations Using Methanol-Stabilized Alkaline Picrate Reagent and Freshly-Prepared Non-Stabilized Alkaline Picrate Reagent

| Day | Solution | Stabilized Reagent: Measured Absorbance | Stabilized Reagent: Calculated Concentration (mg/dl) | Unstabilized Reagent: Measured Absorbance | Unstabilized Reagent: Calculated Concentration (mg/dl) |
|---|---|---|---|---|---|
| 156 | unknown | 0.17 | 5.1 | 0.17 | 5.3 |
| 181 | 1.0 std. | 0.038 | — | 0.045 | — |
| 181 | unknown | 0.040 | 1.1 | 0.052 | 1.2 |
| 181 | unknown | 0.17 | 4.6 | 0.205 | 4.6 |
| 187 | 1.0 std. | 0.037 | — | 0.032 | — |
| 187 | unknown | 0.06 | 1.6 | 0.055 | 1.5 |
| 187 | 5.2 control | 0.20 | 5.4 | 0.20 | 5.6 |
| 187 | unknown | 0.05 | 1.3 | 0.05 | 1.4 |
| 187 | unknown | 0.08 | 2.2 | 0.085 | 1.9 |
| 187 | 5.2 control | 0.20 | 5.4 | 0.23 | 5.2 |
| 191 | 1.0 std. | 0.036 | — | 0.032 | — |
| 191 | unknown | 0.15 | 4.2 | 0.14 | 4.4 |
| 191 | 5.2 control | 0.20 | 5.5 | 0.18 | 5.6 |
| 223 | 1.0 std. | 0.04 | — | 0.039 | — |
| 223 | unknown | 0.20 | 5.0 | 0.18 | 4.6 |
| 223 | 5.2 control | 0.21 | 5.6 | 0.197 | 5.0 |
| 251 | 1.0 std. | 0.039 | — | 0.035 | — |
| 251 | unknown | 0.040 | 1.0 | 0.039 | 1.1 |
| 267 | 1.0 std. | 0.038 | — | 0.035 | — |
| 267 | unknown | 0.038 | 1.0 | 0.036 | 1.1 |
| 330 | 1.0 std. | 0.04 | — | 0.032 | — |
| 330 | 5.2 control | 0.21 | 5.2 | 0.15 | 4.7 |
| 370 | 1.0 std. | 0.043 | — | — | — |
| 370 | 5.2 control | 0.25 | 5.8 | — | — |
| 499 | 1.0 std. | 0.033 | — | — | — |
| 499 | 5.2 control | 0.29 | 5.5 | — | — |

Although the invention has been exemplified by specifically-identified reagent concentrations and reaction conditions, it is to be emphasized that alcohol employed according to the invention will stabilize alkaline picrate solutions containing any realizable concentrations of picrate and base. The invention is not to be limited except by the scope of the appended claims.

I claim:

1. An improved method for determining creatinine, comprising the following steps:

preparing a stabilized alkaline picrate reagent solution by mixing water, picric acid, a molar excess relative to said picric acid of an alkali metal hydroxide, and an alcohol having 1 to 4 carbon atoms, said alcohol being employed in an amount effective to stabilize said alkaline picrate reagent solution during storage;

storing said stabilized alkaline picrate reagent solution in a sealed container for a time in excess of the time an unstabilized alkaline picrate reagent solution otherwise corresponding to said stabilized alkaline picrate reagent solution but lacking said alcohol would be stable, until said stabilized alkaline picrate reagent solution is needed for a creatinine determination;

combining an aliquot of said stored stabilized alkaline picrate reagent solution and an aliquot of a sample solution to be analyzed for creatinine, to produce a colored solution; and measuring the absorbance of said colored solution.

2. The method of claim 1 wherein said alcohol is selected from the group consisting of methanol, ethanol, n-propanol, isopropanol, n-butanol and isobutanol.

3. The method of claim 1 wherein said alcohol is methanol.

4. The method of claim 1 wherein said alcohol is employed in said stabilized alkaline picrate reagent solution at a level of between 5 and 20% by volume.

5. The method of claim 1 wherein said alcohol is employed in said stabilized alkaline picrate reagent solution at a level of approximately 10% by volume.

6. An improved method for determining creatinine, comprising the following steps:

combining in a second environment an aliquot of a sample solution to be analyzed for creatinine and an aliquot of a premixed stabilized alkaline picrate reagent solution previously stored in a first environment; said reagent solution consisting essentially of water, picric acid, a molar excess relative to said picric acid of an alkali metal hydroxide, and an alcohol having 1 to 4 carbon atoms; said alcohol being employed in an amount effective to stabilize said reagent solution during storage; the combination of said sample solution and said reagent solution producing a colored solution; and measuring the absorbance of said colored solution.

7. The method of claim 6 wherein said alcohol is selected from the group consisting of methanol, ethanol, n-propanol, isopropanol, n-butanol and isobutanol.

8. The method of claim 6 wherein said alcohol is methanol.

9. The method of claim 6 wherein said alcohol is employed in said reagent solution at a level of between 5 and 20% by volume.

10. The method of claim 6 wherein said alcohol is employed in said reagent solution at a level of approximately 10% by volume.

* * * * *

UNITED STATES PATENT AND TRADEMARK OFFICE
CERTIFICATE OF CORRECTION

PATENT NO. : 4,818,703
DATED : April 4, 1989
INVENTOR(S) : John M. Pizzolante

It is certified that error appears in the above-identified patent and that said Letters Patent is hereby corrected as shown below:

Column 2, line 54, "picric solutions," should read --picric acid solutions,--.

Column 3, line 34, "n-propanol, n-butanol," should read --n-propanol, isopropanol, n-butanol,--.

Column 4, line 1, "experimenrtal" should read --experimental--.

Signed and Sealed this

Fifteenth Day of January, 1991

*Attest:*

HARRY F. MANBECK, JR.

*Attesting Officer*  *Commissioner of Patents and Trademarks*